United States Patent [19]

Banno et al.

[11] Patent Number: 4,498,780
[45] Date of Patent: Feb. 12, 1985

[54] PHOTOMETERING APPARATUS FOR USE IN CHEMICAL ANALYZER

[75] Inventors: Taiichi Banno; Kazuo Hijikata, both of Hachioji; Hiroshi Takekawa, Sagamihara, all of Japan

[73] Assignee: Olympus Optical Co., Ltd., Tokyo, Japan

[21] Appl. No.: 345,052

[22] Filed: Feb. 2, 1982

[30] Foreign Application Priority Data

Feb. 10, 1981 [JP] Japan .................................. 56-17391

[51] Int. Cl.³ ..................... G01N 21/27; G01N 21/01
[52] U.S. Cl. .................................... 356/414; 356/244; 356/440
[58] Field of Search ............... 356/246, 440, 414, 244; 422/109, 186; 250/576

[56] References Cited

U.S. PATENT DOCUMENTS

| 3,656,833 | 4/1972 | Wallace | 356/246 X |
| 3,999,862 | 11/1975 | Revillet et al. | 250/573 X |
| 4,004,150 | 1/1977 | Natelson | 356/246 X |
| 4,224,405 | 9/1980 | Hijikara | 356/436 X |
| 4,240,751 | 12/1980 | Linnecke | 356/440 X |
| 4,254,223 | 3/1981 | Schuurs et al. | 356/440 X |
| 4,397,560 | 8/1983 | Andresen | 356/440 |

FOREIGN PATENT DOCUMENTS 113383 2/1978 Japan .

Primary Examiner—Vincent P. McGraw
Attorney, Agent, or Firm—Parkhurst & Oliff

[57] ABSTRACT

A photometering apparatus for use in a chemical analyzer of multi-channel type includes a liquid type thermostat made of transparent material and a block made of transparent material and movably mounted on a bottom wall of the thermostat, a number of reaction vessels being constituted by depressions formed in said block in a matrix form. An absorption of a test liquid contained in respective reaction vessels on each channel is measured by projecting a light beam emitted from a light source incident perpendicularly upon the test liquid and by receiving the light beam transmitted through the test liquid, a bottom portion of the reaction vessel and the bottom wall of thermostat.

11 Claims, 4 Drawing Figures

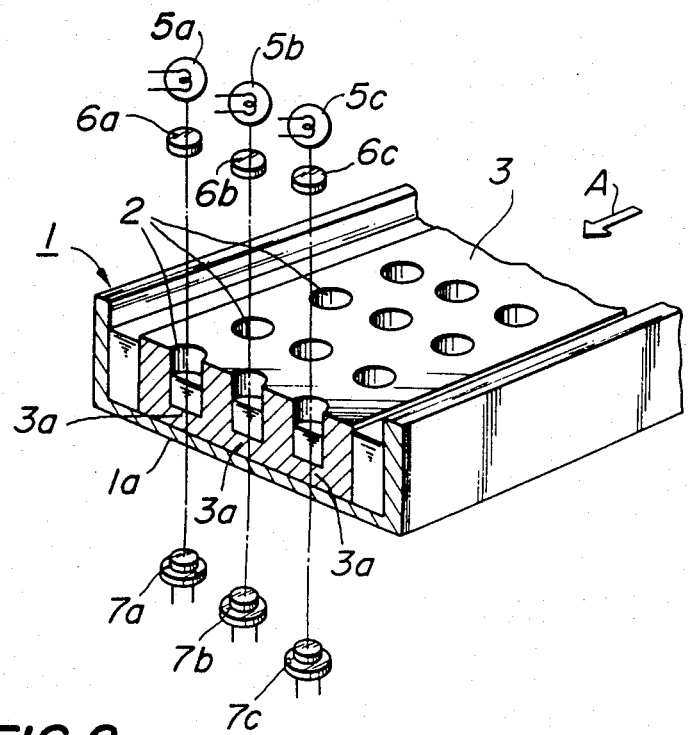
FIG_1
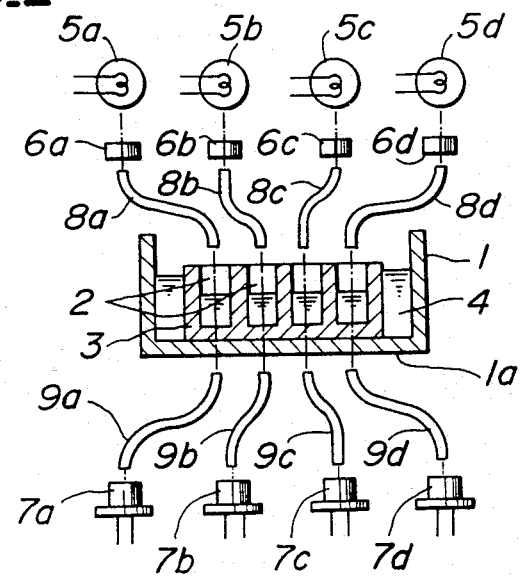
FIG_2

PHOTOMETERING APPARATUS FOR USE IN CHEMICAL ANALYZER

BACKGROUND OF THE INVENTION

The present invention relates to a photometering apparatus for use in a chemical analyzer, and more particularly to a photmetering apparatus of a direct measuring type in which a colorimetric measurement of a test liquid is effected, while the test liquid is still contained in a reaction vessel.

There have been proposed various kinds of such a direct measuring type photometering apparatus. For instance, in a Japanese Patent Application Laid-open Publication No. 113,383/76, there is disclosed a photometering apparatus in which a reaction vessel made of transparent material is arranged in a thermostat of an air-bath type and an absorption of a test liquid contained in the reaction vessel is measured by transmitting a measuring light beam through side walls of the reaction vessel. However, the thermostat of air-bath type cannot keep a desired temperature in a prompt and precise manner as compared with a liquid type thermostat and thus, a time required for effecting the photometry is liable to be long and further a high measuring accuracy could hardly be obtained. In order to overcome such a drawback one may consider to use the liquid type thermostat instead of the air-bath type thermostat. However, in such a case the photometry has to be performed through a liquid in the thermostat and thus, the high accuracy of measurement could not be attained due to absorption in the temperature conrolled liquid in the thermostat.

Further, in the known apparatus, since the measuring light beam is passed through the side walls of reaction vessel in a radial direction, dimension of the reaction vessel should be made accurate in order to obtain an accurate length of an optical path and therefore, a cost for manufacturing the reaction vessel becomes high. Moreover, in case of a multi-channel analyzer, the reaction vessels in adjacent channels should be separated by a relatively large distance in order to eliminate mutual interference, and this results in that the apparatus is liable to be large in size. Moreover, an optical system of a photometering unit is liable to be complicated and a loss of light becomes large to decrease the measurement precision.

In a U.S. Pat. No. 3,999,862, there is described a photometering apparatus of quasi-direct type. In this apparatus, a reaction vessel and a photometric cell are formed integrally into a single vessel and a test liquid is transferred from the reaction vessel to the photometric cell by means of centrifugal force. However, this apparatus could not be applied to the multi-channel analyzer and has a low processing ability, because the test liquids could not be treated continuously. Further, since use is made of the centrifugal force, a driving mechanism becomes complicated and expensive. Moreover, the photometry has to be effected during the rotation, a data process becomes extremely cumbersome. Since a temperature regulating liquid is transferred to the photometric cell by means of the centrifugal force and thus, the photometric cell is exposed, while the rotor is not rotated, the temperature of the test liquid could not be regulated well and a measuring error is introduced.

In addition to the direct measuring type explained above, a flow cell type photmetering apparatus has been proposed. However, in the flow cell type apparatus, since the test liquid must be transferred from the reaction vessel to a flow cell by sucking force, a substantial amount of the test liquid is required. In recent, a quite large number of test items have to be effected for respective samples and to this end an amount of the test liquid should be corresponding small. The flow cell type apparatus does not satisfy such a requirement. Further, since the flow cell has to be used for successive test liquids, there occurs a problem of contamination to decrease the measuring precision. In order to avoid the contamination, there must be provided a complicated mechanism for washing the flow cell.

SUMMARY OF THE INVENTION

The present invention has for its object to provide a novel photometering apparatus which can obviate the above mentioned drawbacks of the known apparatuses and can utilize a liquid type thermostat which can keep the test liquid at a desired temperature in a prompt and accurate manner.

It is still another object of the invention to provide a photometering apparatus which can attain a high accuracy of measuremennt without a measuring light beam passing through a temperature controlled liquid in the thermostat.

It is still another object of the invention to provide a photometering apparatus which can be made simple in construction, can be manufactured cheaply and can be advantageously applied to a multi-channel analyzer.

According to the invention, a photometering apparatus for use in a chemical analyzer comprises a liquid type thermostat containing a temperature controlled liquid and having a bottom wall made of transparent material;

a plurality of reaction vessels arranged in said thermostat and having bottom walls made of transparent material; and a photometering unit including at least one light source for emitting a light beam and at least one light receiving element for receiving the light beam emitted from the light source and transmitted through test liquids contained in the reaction vessels, the light source and light receiving element being so arranged that they have an optical axis extending perpendicularly to a surfce of said test liquids through the bottom walls of said thermostat and reaction vessels.

BRIEF DESCRIPTION OF THE DRAWINGS

FIG. 1 is a perspective view showing an embodiment of the photometering apparatus according to the invention;

FIG. 2 is a cross section illustrating a modified embodiment of the photometering apparatus according to the invention;

DESCRIPTION OF THE PREFERRED EMBODIMENTS

Figure 3:
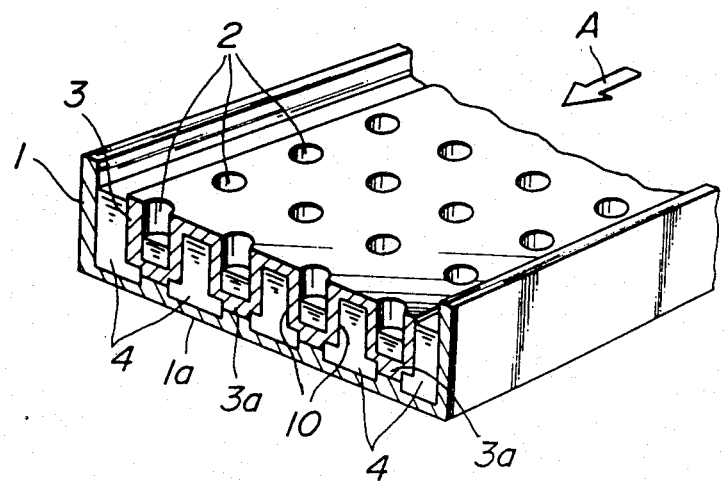
FIG. 3 is a perspective view depicting another embodiment of the photometering apparatus according to the invention.

FIG. 1 is a perspective view showing an embodiment of the photometering apparatus according to the invention. In the present embodiment, the photometering apparatus comprises a liquid type thermostat 1 in which is arranged a block 3 having a number of reaction vessels 2 formed therein in a matrix form. The analyzer of the embodiment is of a three-channel type. The block 3 may be formed by molding of transparent plastics. The block 3 is directly placed on a bottom wall 1a of the thermostat 1 and can be slid on the bottom wall 1a in a direction shown by an arrow A. In the thermostat 1 is contained a temperature controlled liquid 4 for keeping test liquids in the reaction vessels 2 at a desired temperature. According to the invention, the regulating liquid 4 does not penetrate between the bottom wall 1a of thermostat and the block 3.

At a suitable position in a travelling path of the block 3, are arranged a plurality of light sources 5a, 5b and 5c, filters 6a, 6b and 6c and light receiving elements 7a, 7b and 7c in such a manner that light beams emitted from the light sources and transmitted through the filters are made perpendicularly incident upon the test liquids in the reaction vessels. The filters 6a, 6b and 6c have desired spectral transmitting properties for effecting predetermined test items. The light beams impinging upon the test liquids are transmitted through bottom portions 3a of the reaction vessels and the bottom wall 1a of thermostat 1 and are made incident upon the light receiving elements 7a, 7b and 7c, respectively. To this end, at least light transmitting parts of the bottom wall 1a of thermostat must be made of transparent material. In this embodiment, the thermostat 1 is wholly made of transparent material. In this manner, absorption of the test liquids contained in the reaction vessels 2 can be successively measured. In this case, since the reaction vessels 2 are dipped in the regulating liquid 4, the test liquids can be heated promptly and accurately to a desired temperature. Further, the measuring light beams are not transmitted through the liquid 4 and thus, the very accurate measurement can be effected. Moreover, according to the invention, the measuring light beams are made perpendicularly incident upon the test liquids and therefore, any variation in amounts of the test liquids does not substantially affect the measurement due to the following fact. An absorption A of the test liquid is generally expressed by the following equation, wherein k is a coefficient.

$$A = k \times (\text{concentration}) \times (\text{light path})$$
$$= k \times (\text{sample amount}) \times (\text{light path}) / (\text{total amount of test liquid})$$
$$= k \times (\text{sample amount}) \times (\text{light path}) / (\text{cross sectional area}) \times (\text{light path})$$
$$= k \times (\text{sample amount}) / (\text{cross sectional area})$$

In this equation, the sample amount is much smaller than amounts of diluent, reagent, etc. and can be considered to be substantially constant. Therefore, any variation in the total amount of the test liquid, and thus the light path do not affect the measurement of absorption.

FIG. 2 shows a modified embodiment of the photometering apparatus illustrated in FIG. 1. In this embodiment, the construction of the liquid type thermostat 1 and block 3 is similar to that shown in FIG. 1, but a space between the reaction vessels in the adjacent channels is made much shorter and thus, a smaller multi-channel analyzer can be realized. In such a construction, there could not be attained sufficient spaces for arranging light sources 5a to 5d, filters 6a to 6d and light receiving elements 7a to 7d. Therefore, between the filters and the reaction vessels 2, and between the reaction vessels and the light receiving elements are arranged optical fibers 8a to 8d and 9a to 9d, respectively. By means of the optical fibers, the light sources, filters and light receiving elements can be arranged separately without causing any interference therebetween.

FIG. 3 is a perspective view showing another embodiment of the photometering apparatus according to the invention. In this embodiment, in order to regulate the temperature of the test liquids much more precisely, the liquid 4 is made in contact with respective reaction vessels 2. For this purpose, in the block 3 are formed recesses 10 from the bottom wall of the block and the liquid 4 is circulated through these recesses 10. Since the recesses 10 extend along the channel at intermediate portions between successive channels, the bottom walls 3a of the reaction vessels 2 are directly made in contact with the bottom wall 1a of thermostat 1, no liquid is interposed therebetween.

Figure 4:
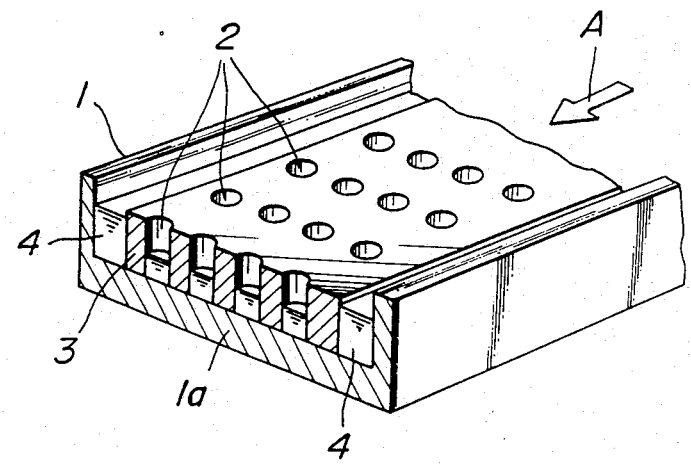
FIG. 4 is a perspective view showing still another embodiment of the photometering apparatus according to the invention.

FIG. 4 is a perspective view illustrating still another embodiment of the photometering apparatus according to the invention. In this embodiment, in the block 3 are formed a number of holes which constitute reaction vessels 2 together with a bottom wall 1a of a liquid type thermostat 1. To this end, the block 3 is placed on the bottom wall 1a. In order to avoid a possible leakage of test liquids contained in the reaction vessels 2, there may be inserted suitable sealing members between the block 3 and the bottom wall 1a. In this embodiment, the bottom wall 1a of thermostat serves as the bottom walls of the reaction vessels and thus, the block 3 may be wholly made of opaque material. Moreover, since there is no possibility that the liquid 4 is penetrated into the optical path, the measurement is not affected by the liquid 4 at all.

The present invention is not limited to the embodiments explained above, but may be modified or changed in various ways. For instance, in the above embodiments, the block 3 is movably placed on the bottom wall 1a of thermostat, but they may be cemented together. In this case the assembly of the block 3 and the thermostat 1 must be moved in a given direction. Such a construction is particularly advantageous in the embodiment shown in FIG. 4. In the above embodiments, all the reaction vessels 2 are formed in the single block 3, but the block may be composed of a plurality of block sections cut in a direction parallel or perpendicular to the channel direction. In such a construction, the regulating liquid of the thermostat may be introduced between adjacent block sections and therefore, the efficiency of the thermostat can be further increased. According to the invention, since the measuring light beams are not transmitted through the side walls of reaction vessels, a shape of cross section of the reaction vessel may be any desired shape such as circle, triangle, rectangle, polygonal and combinations thereof. The bottom wall of the reaction vessel is not always made flat, and for instance, a peripheral portion may be curved. In such a construction, an amount of liquid remained in the reaction vessel after discharging operation can be reduced. In any case, it is preferable to make a portion of the reaction vessel bottom wall flat through which flat portion the measuring light beam is transmitted. With respect to the photometery unit, the filters may be replaced by diffraction gratings, and the filters or gratings may be arranged between the reaction vessels and the light receiving elements. Moreover, the positions of the light sources and light receiving elements may be inverted up side down. In the about embodiments, the photometering optical paths for the channels are made identical with each other, but may be situated at different positions viewed in the channel direction. As a case may be, a plurality of photometering optical axes may be provided in a single channel. In this case, a plurality of photometering positions are arranged in the channel direction. In a modified embodiment of the apparatus shown in FIG. 4, the reaction vessels having its own bottom walls may be plugged into openings formed in the bottom wall of thermostat. In case of using a clear and degassed liquid for the thermostat, the liquid may be introduced into spaces between the bottom walls of reaction vessels and the bottom wall of thermostat. In such a construction, the reaction vessels may be secured to or integrally formed with a frame having apertures formed therein and the frame may be movably placed on the bottom wall of thermostat. The regulating liquid may be circulated through the apertures of the frame.

As explained above, according to the invention, since the test liquids are heated by the temperature controlled liquid having a large heat capacity, the test liquids can be heated speedily to given temperature and are not affected by variation in temperature of surrounding atmosphere. Moreover, unevenness of temperature can be eliminated and temperature control can be effected precisely. Further, the measuring light beam is made incident upon the test liquid perpendicularly and thus the measurement could never be influenced by errors in dimension of the reaction vessels and an amount of the test liquids. Therefore, the reaction vessels can be manufactured in a cheap manner. Since the space between adjacent channels can be reduced, the multi-channel analyzer can be made small in size. Moreover, the direct measurement is effected and thus, the amounts of the test liquids can be reduced materially and any contamination between the test liquids can be avoided.

What is claimed is:

1. A photometering apparatus for use in a chemical analyzer comprising
   a liquid type thermostat containing a temperature controlled liquid and having a bottom wall made of transparent materials;
   a plurality of reaction vessels arranged in said thermostat and having bottom walls made of transparent material, the bottom walls of the reaction vessels contacting the bottom wall of the thermostat; and
   a photometering unit including at least one light source for emitting a light beam and at least one light receiving element for receiving the light beam emitted from the light source and transmitted through test liquids contained in the reaction vessels, the light source and light receiving element being so arranged that they have an optical axis extending perpendicularly to a surface of said test liquids through the bottom walls of said thermostat and reaction vessels.

2. An apparatus according to claim 1, wherein said reaction vessels are arranged in said thermostat in a matrix form so as to constitute a plurality of channels.

3. An apparatus according to claim 2, wherein said photometering unit compreses a plurality of sets of said light source and light receiving element, each set being provided for respective channels.

4. An apparatus according to claim 3, wherein a filter is inserted in an optical path of each set of said light source and light receiving element.

5. An apparatus according to claim 3, wherein optical fibers are arranged between the light sources and the reaction vessels and between the reaction vessels and the light receiving elements.

6. An apparatus according to claim 1, wherein said reaction vessels are constituted by depressions formed in a block made of transparent material and said block is mounted on the bottom wall of the thermostat.

7. An apparatus according to claim 1, wherein said reaction vessels are constituted by holes formed in a block arranged on the bottom wall of thermostat.

8. An apparatus according to claim 6 or 7, wherein said block is slidably placed on the bottom wall of thermostat.

9. An apparatus according to claim 6 or 7, wherein said block is secured to the bottom wall of thermostat.

10. An apparatus according to claim 6, wherein said block is mounted on the bottom wall of thermostat by means of a frame member having openings formed therein and the temperature controlled liquid in the thermostat is circulated through said openings in the frame member.

11. An apparatus according to claim 6, wherein said block has at least one recess formed from a bottom surface of the block and said temperature controlled liquid is circulated through said recess.

* * * * *